(12) United States Patent
Robertson

(10) Patent No.: US 12,419,577 B2
(45) Date of Patent: Sep. 23, 2025

(54) MULTI-BODY EARPIECE

(71) Applicant: NextSense, Inc., Mountain View, CA (US)

(72) Inventor: Nicholas Robertson, Mountain View, CA (US)

(73) Assignee: NEXTSENSE, INC., Mountain View, CA (US)

( * ) Notice: Subject to any disclaimer, the term of this patent is extended or adjusted under 35 U.S.C. 154(b) by 138 days.

(21) Appl. No.: 17/995,845

(22) PCT Filed: May 11, 2021

(86) PCT No.: PCT/IB2021/053972
§ 371 (c)(1),
(2) Date: Oct. 7, 2022

(87) PCT Pub. No.: WO2021/205422
PCT Pub. Date: Oct. 14, 2021

(65) Prior Publication Data
US 2023/0148963 A1    May 18, 2023

Related U.S. Application Data

(63) Continuation of application No. 16/842,163, filed on Apr. 7, 2020, now abandoned.

(51) Int. Cl.
*A61B 5/00* (2006.01)
*H04R 1/10* (2006.01)

(52) U.S. Cl.
CPC .......... *A61B 5/6817* (2013.01); *A61B 5/0024* (2013.01); *H04R 1/1016* (2013.01); *A61B 2562/02* (2013.01); *H04R 2201/10* (2013.01)

(58) Field of Classification Search
CPC . A61B 5/6817; A61B 5/0024; A61B 2562/02; A61B 5/01; A61B 5/02438;
(Continued)

(56) References Cited

U.S. PATENT DOCUMENTS

| | | | |
|---|---|---|---|
| 5,048,090 A * | 9/1991 | Geers .................... | H04R 25/607 381/328 |
| 7,899,200 B2 * | 3/2011 | Karamuk ............. | H04R 25/656 381/328 |

(Continued)

FOREIGN PATENT DOCUMENTS

KR    20170122305 A * 11/2017 ............. G06F 1/163

*Primary Examiner* — Angelica M McKinney
(74) *Attorney, Agent, or Firm* — Jason A. Smith; Shumaker, Loop & Kendrick, LLP

(57) ABSTRACT

The technology provides a multi-body earpiece suitable for use as an in-ear sensor system, which can be used for biometrics or a human-computer interface. The multi-body earpiece includes two body elements connected together by a flexure. These components provide at least 3 points of contact along different parts of the outer ear, in which the flexure is tethered to the two bodies and arranged to lock them in place during wear. In addition to having stability from moving while minimizing sound occlusion, this arrangement enables any electrodes for the on-board sensor(s) to remain in contact with the skin of the ear, and provide as many contact points in desired areas as the electronics dictate for the signals of interest.

18 Claims, 11 Drawing Sheets

(58) Field of Classification Search
CPC ... A61B 5/0533; A61B 5/1114; A61B 5/1116; A61B 5/14532; A61B 5/14551; A61B 5/245; A61B 5/291; A61B 5/384; A61B 5/002; A61B 5/6803; A61B 2562/0219; A61B 5/721; H04R 1/1016; H04R 2201/10; H04R 1/105; H04R 2420/07; H04R 1/1091; H04R 25/652; H04R 25/656; H04R 25/607; G16H 40/67; G01R 33/072

See application file for complete search history.

(56) References Cited

U.S. PATENT DOCUMENTS

| | | | | |
|---|---|---|---|---|
| 8,374,367 | B2 * | 2/2013 | Nielsen | H04R 25/652 |
| | | | | 381/328 |
| 8,792,663 | B2 * | 7/2014 | Cano | H04R 1/1016 |
| | | | | 381/328 |
| 9,736,569 | B2 * | 8/2017 | Kelly | H04R 25/652 |
| 9,838,771 | B1 * | 12/2017 | Masaki | G01R 33/072 |
| 10,034,078 | B2 * | 7/2018 | Silvestri | H04R 1/1091 |
| 10,973,415 | B2 * | 4/2021 | LeBoeuf | G16H 40/67 |
| 2001/0043707 | A1 * | 11/2001 | Leedom | H04R 25/65 |
| | | | | 381/328 |
| 2009/0180654 | A1 * | 7/2009 | Nielsen | H04R 25/656 |
| | | | | 381/328 |
| 2015/0366475 | A1 * | 12/2015 | Just | A61B 5/721 |
| | | | | 600/300 |
| 2018/0242068 | A1 * | 8/2018 | Kelley | H04R 1/105 |

* cited by examiner

150

100

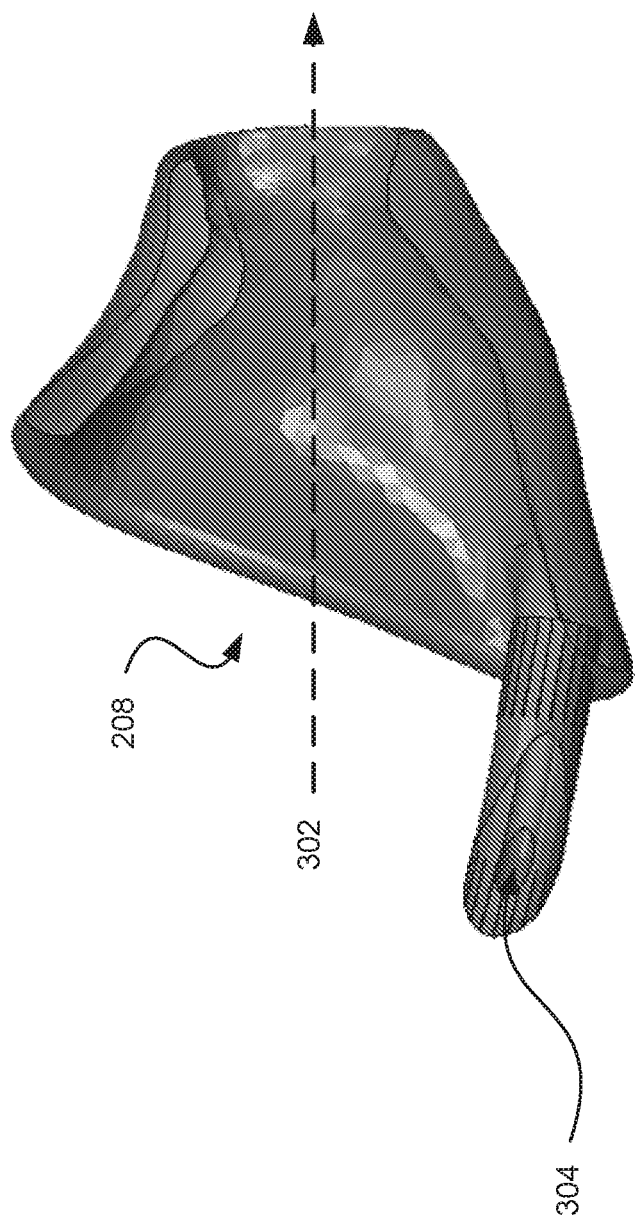

400

620

610

600

710

700

MULTI-BODY EARPIECE

This application claims priority to U.S. application Ser. No. 16/842,163, filed on Apr. 7, 2020, the disclosure of which is hereby incorporated by reference herein in its entirety.

BACKGROUND

Wearable sensors have been used to detect bio signals, such as electroencephalogram (EEG) signals, from the wearer's body. These signals can be used for medical or non-medical (e.g., brain control interface) purposes. In the past, caps have been worn on the user's head to capture EEG signals. These caps can capture input via multiple data channels. However, wearing a cap for an extended period of time can be cumbersome and uncomfortable. It can also be difficult to obtain high quality signals, especially if the wearer has thick hair. In-ear sensors, for instance using custom-molded earpieces, have also been considered. Unfortunately, even a custom in-ear sensor assembly may have various drawbacks, including difficulty providing a stable arrangement that is both securely and comfortably maintained in the ear. Other issues can include partially or completely blocking ambient sounds, as well as costly and labor-intensive manufacturing techniques.

BRIEF SUMMARY

The technology relates to a multi-body earpiece suitable for use as an in-ear sensor system, which can be used for biometrics such as an EEG or magnetoencephalograph (MEG) signal detection, or a human-computer interface. The multi-body earpiece includes two or more elements connected together by a flexure. The elements and flexure provide at least 3 points of contact along different parts of the outer ear, in which the flexure is arranged to lock the two elements in place.

Such an arrangement minimizes the amount of material required for the sensor system, while providing a secure-fitting device that can be worn for hours, days or longer in order to provide maximal benefit to the wearer. The arrangement is able to minimize the occlusion of ambient sound so the wearer can easily hear what is going on around him or her, while being comfortable and as unobtrusive as possible.

According to one aspect, a multi-body earpiece assembly configured for partial or complete insertion in an ear of a wearer is provided. The sensor assembly comprises a first body, a second body, a flexure and one or more sensors. The first body is configured to be at least partly received within the cymba conchæ region of the ear. The second body is configured to be received along the opening to the ear canal. The flexure is coupled to the first body at a first end of the flexure and to the second body at a second end of the flexure. Each of the first body, the second body and the flexure provides a point of contact along a different portion of the ear to retain the multi-body earpiece in an operational position. The one or more sensors are disposed along the multi-body earpiece assembly, and are configured to detect bio-signals via the ear of the wearer.

The flexure may be configured to conform to a portion of the concha along an underside of the antihelix of the ear when in the operational position. The one or more sensors may be disposed along the first and second bodies. The second body may be configured to avoid sound occlusion when the multi-body earpiece is worn in the ear of the wearer. Here, a housing of the second body may define a central opening therethrough to avoid the sound occlusion.

The flexure may be configured so that the first and second ends are moveable toward and away from one another. In this case, the flexure may be arranged to flex or rotate while conforming to a portion of the concha along an underside of the antihelix of the ear. The flexure may have a hollow interior from the first end to the second end. The flexure may have a tension that is tunable by adjusting a length of the flexure. The flexure may be a separate component insertable into the first body and the second body. A tension or stiffness of the flexure may be tunable based on a thickness of the flexure.

In one example, the multi-body earpiece further comprises circuitry attached to one or more of the first body, the second body and the flexure. The circuitry is operatively coupled to the one or more sensors. The circuitry includes a processing device configured to receive the detected bio-signals from the one or more sensors and to perform on-board processing of the received bio-signals or to transmit the received bio-signals to a remote processing system.

The multi-body earpiece may be formed of multiple materials including a first material having a first hardness and a second material having a second hardness less than the first hardness. The materials may include one or more bio-compatible materials arranged along the first body and the second body.

According to another aspect of the technology, a sensor system is configured to detect and process bio signals of a wearer. The sensor system comprises the multi-body earpiece as described in any of the above examples, as well as a remote processing system. The remote processing system includes a transceiver configured for communication with a transceiver of the multi-body earpiece. The remote processing system also includes one or more processors configured to process the bio signals received from the multi-body earpiece. The system may include a pair of multi-body earpieces, wherein a first one of the pair is configured for insertion into one ear of the wearer and a second one of the pair is configured for insertion into the other ear of the wearer.

In one example, the flexure is configured to conform to a portion of the concha along an underside of the antihelix of the ear when in the operational position. The one or more sensors may be disposed along the first and second bodies.

The sensor system may further comprise circuitry attached to one or more of the first body, the second body and the flexure. Here, the circuitry is operatively coupled to the one or more sensors. The circuitry includes a processing device configured to receive the detected bio-signals from the one or more sensors and to perform on-board pre-processing of the received bio-signals prior to transmission to the remote processing system.

Alternatively, the sensor system may further comprise circuitry attached to one or more of the first body, the second body and the flexure, wherein the circuitry is operatively coupled to the one or more sensors, and the circuitry includes a processing device configured to gather the detected bio-signals from the one or more sensors and transmit the gathered signals to the remote processing system.

BRIEF DESCRIPTION OF THE DRAWINGS

FIG. 3 illustrates a cross-sectional view of one body of the earpiece of FIGS. 2A-H in accordance with aspects of the technology.

DETAILED DESCRIPTION

Figure 1B:
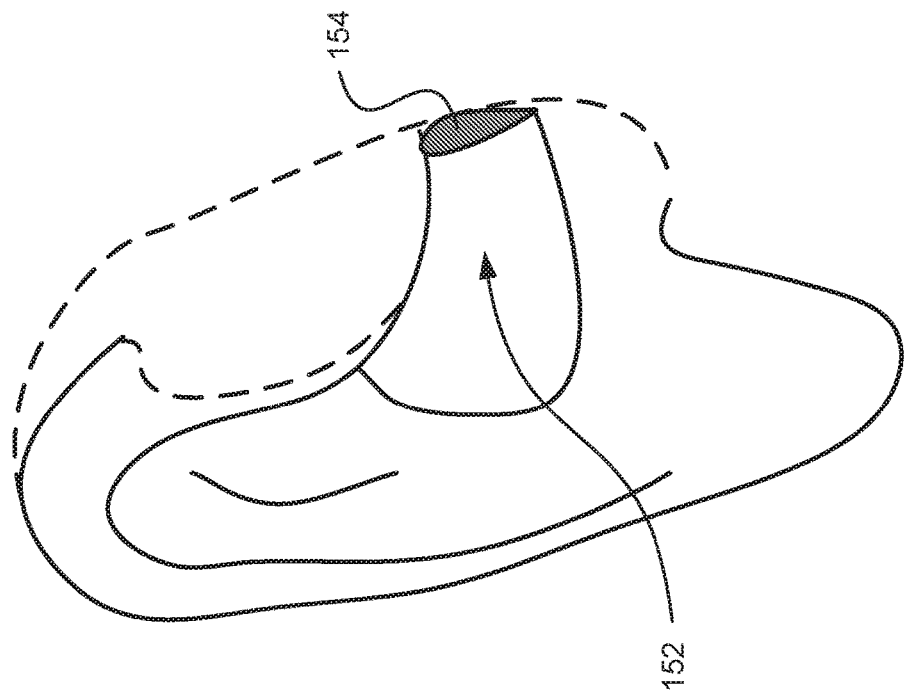
FIGS. 1A-B illustrate an example human ear.

The human ear is a complex organ that includes three main parts, the outer ear, middle ear and inner ear. An example of the outer ear (auricle or pinna) is illustrated in view 100 of FIG. 1A. As shown, the outer ear includes a helix 102, antihelix 104, lobule 106, concha 108, tragus 110 and opening to the ear canal 112. The concha 108 includes an upper region 114a known as cymba conchæ, and a lower region 114b adjacent to the ear canal that is known as the cavum conchæ.

Figure 1A:
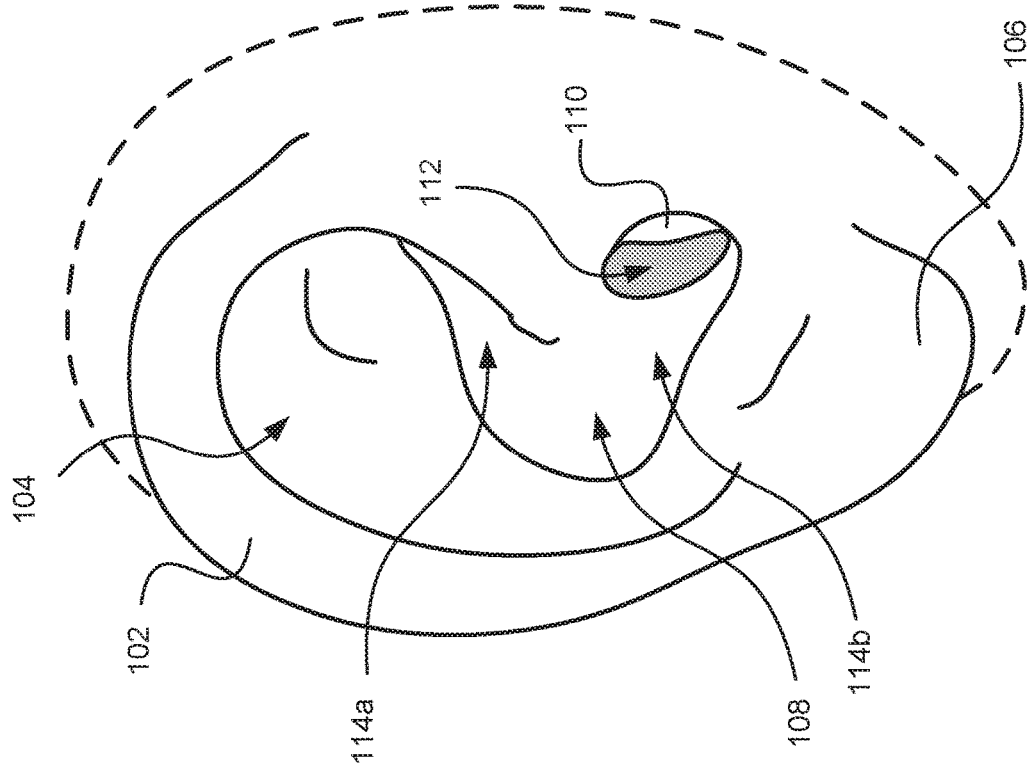

FIG. 1B illustrates another view 150 showing a partial cutaway perspective to illustrate the outer portion of the ear canal 152 leading to the ear drum (tympanic membrane) 154. It can be seen that the outer ear and ear canal are complex, three-dimensional structures. Furthermore, the outer ear is formed of cartilage and skin, which means that it is a flexible organ. Thus, if the person is wearing a hat or helmet, or rolls over in his or her sleep, the shape of the outer ear can change. For instance, the helix and antihelix may fold over, the lobule may be pulled away from or pushed toward the opening of the ear canal, and/or the tragus may be pushed inward towards the ear canal. As a result, an effective in-ear sensor system needs to conform with a malleable 3D shape while providing sufficient points of contact for the on-board sensors.

According to one aspect, a comfortable earpiece is provided that has multiple areas for electronics and sensors for bio-sensing. The conformable earpiece includes spaced-apart elements tethered together via a flexure. The flexure and the discrete elements each help anchor the earpiece within the outer ear, for instance by providing at least three points of contact along different regions of the outer ear. In addition to having stability from moving while minimizing sound occlusion, this arrangement enables any electrodes for the on-board sensor(s) to remain in contact with the skin of the ear, and provide as many contact points in the correct areas as the electronics dictate for the signals of interest. The general architecture is illustrated in the accompanying figures and is discussed further below.

Sensors can be located along various points of the earpiece, such as on the two discrete elements, for use in EEG, MEG or other diagnostic situations. For instance, Alpha waves on the order of 8-12 Hz can be detected either by either EEG or MEG. In addition, lower frequency signals (e.g., Delta waves between 0.5-3 Hz or Theta waves between 3-8 Hz) and/or higher frequency signals (e.g., Beta waves between 12-38 Hz or Gamma waves between 38-42 Hz) may also be detected. One or more of these types of signals can be evaluated and analyzed either alone or in conjunction with other data to provide information (e.g., biomarkers) about the wearer. The other data may be obtained by additional in-ear sensors (e.g., in the same assembly or in a sensor assembly worn in the other ear) or sensors located elsewhere on or near the wearer. These may include heart rate and temperature sensors. Electrodermal activity (EDA) sensors that detect skin potential, resistance, conductance, admittance, or impedance, such as galvanic skin response sensors, may also be employed. Furthermore, a pulse oximeter sensor, a glucometer, orientation sensors, location sensors and/or accelerometers can also be used. These sensors can be used in any combination. The biomarkers or other information can be evaluated to help classify mental or emotional states, as well as activities of daily living.

Example Structures

An in-ear sensor system will now be described in accordance with aspects of the technology.

Figure 2B:
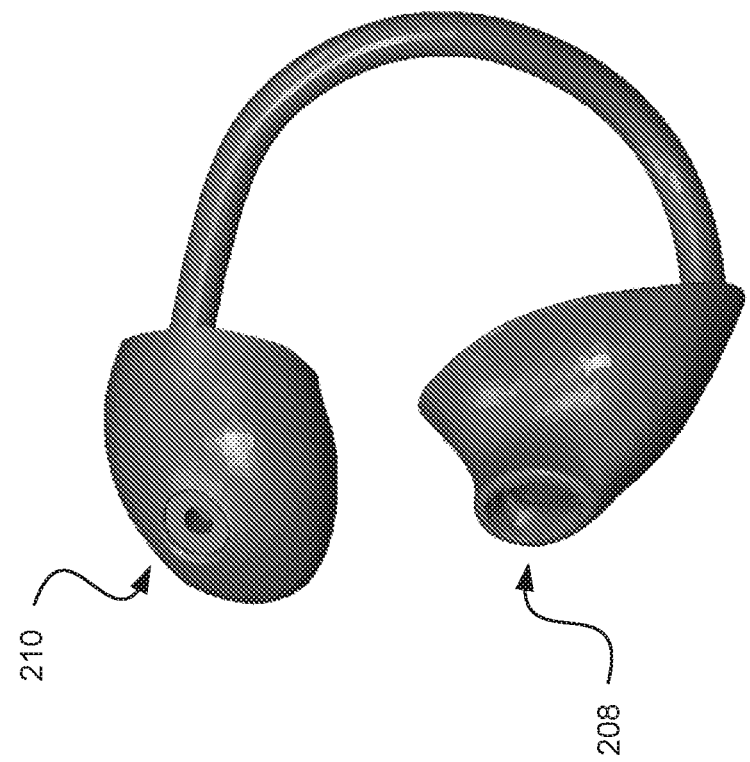
FIGS. 2A-H illustrate an example multi-body earpiece in accordance with aspects of the technology.
Figure 2A:
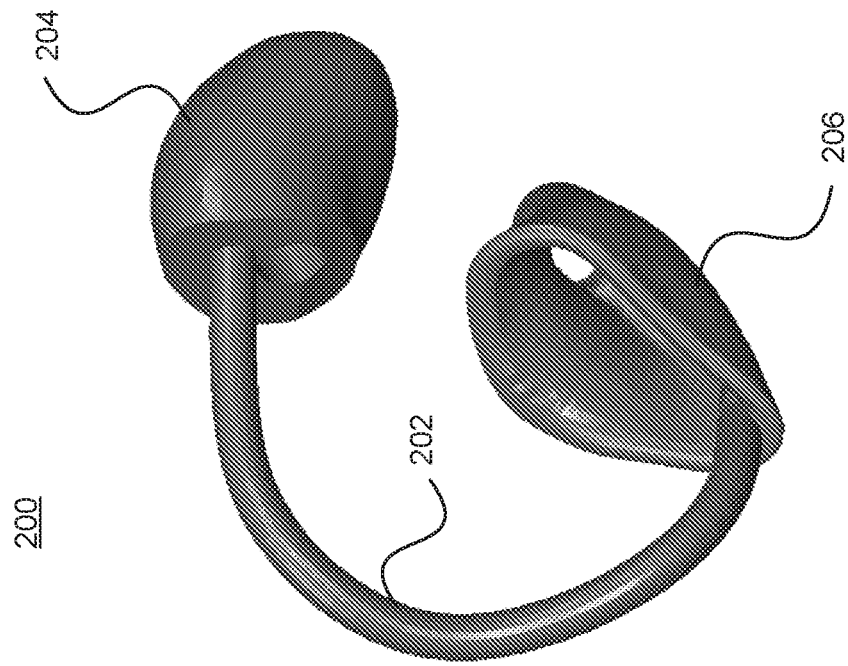
Figure 2D:
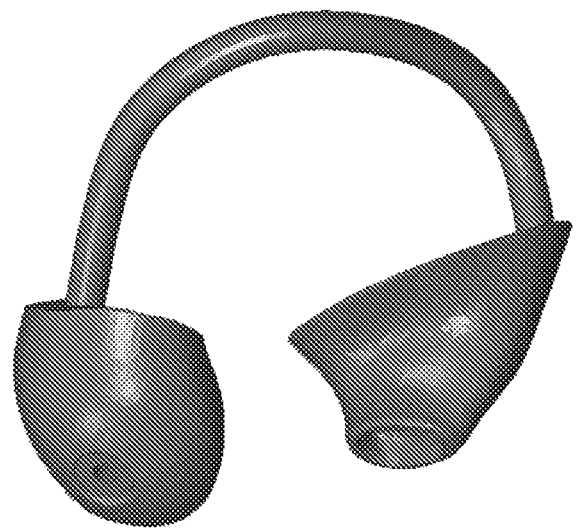
Figure 2C:
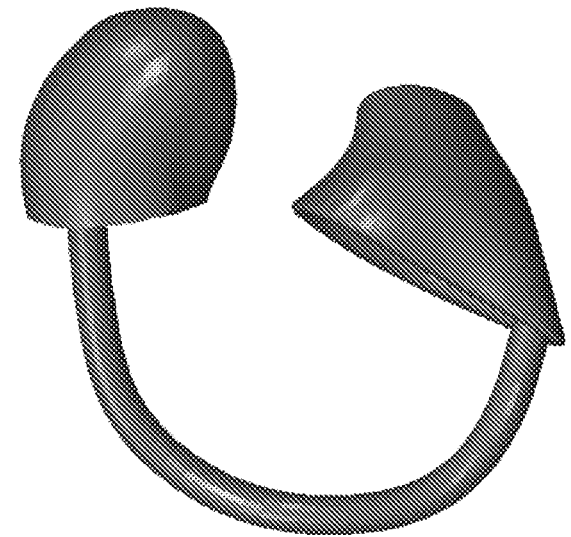
Figure 2H:
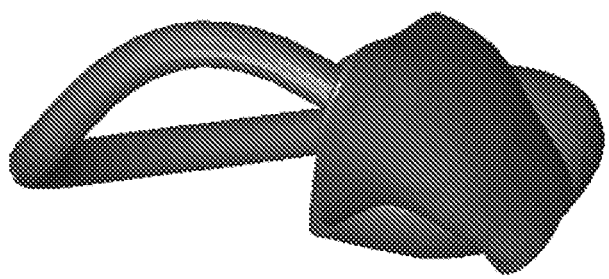
Figure 2G:
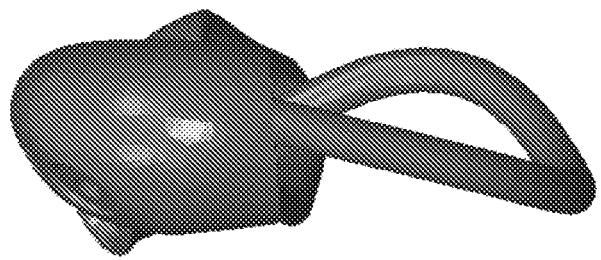
Figure 2F:
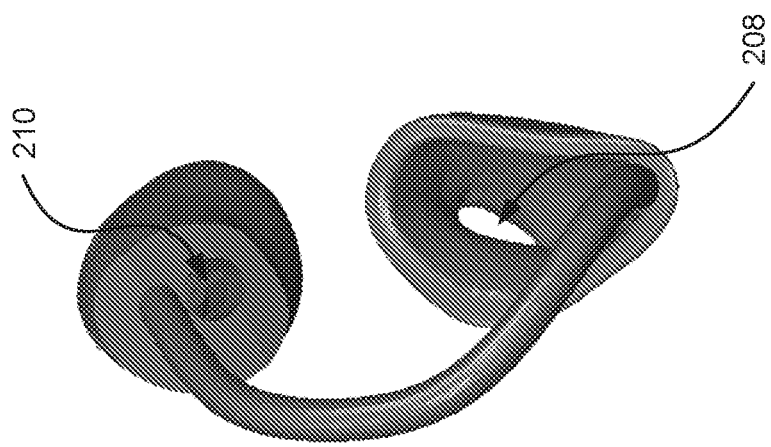
Figure 2E:
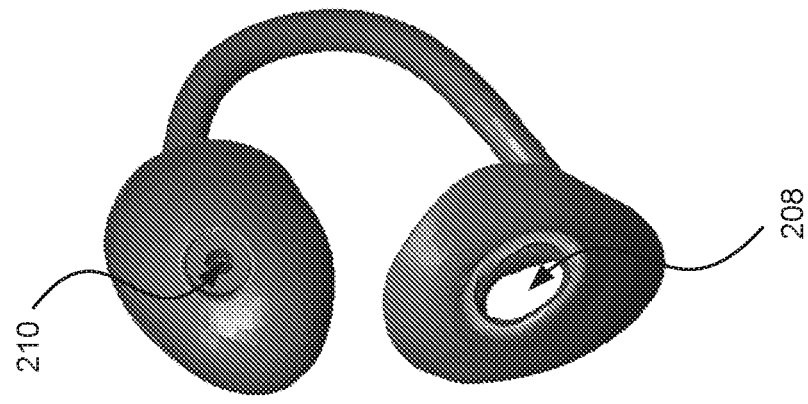

Example multi-body earpiece structure 200 of FIGS. 2A-H has a central flexure affixed at both ends to respective discrete bodies. When placed along the outer ear, the overall structure is "C" shaped, with the flexure curved to fit within along an interior surface of the ear's antihelix. In particular, FIG. 2A is a front perspective view of the side of the example structure, while FIG. 2B is a rear perspective view. FIG. 2C is a front view and FIG. 2D is rear view. FIG. 2E is a right side view and FIG. 2F is a left side view. FIG. 2G is a top view and FIG. 2H is a bottom view.

As shown in FIG. 2A, flexure 202 is a thin, elongated component having one end affixed to a first body 204, and a second end affixed to a second body 206. The flexure 202 has an arcuate shape, for instance for conforming to the portion of the concha along the underside of the antihelix (see FIGS. 5A-B). However, when the earpiece structure is not inserted into the ear, the flexure 202 may be straight, bent, retain the operational arcuate shape or have some other shape. In one scenario, the first body 204 is configured to be received within the cymba conchæ region, while the second body 206 is configured to be received along the opening to the ear canal. The second body may also be partly disposed along the cavum conchæ region immediately adjacent to the ear canal opening.

It may be desirable in many situations to enable the wearer to hear ambient sounds while the sensor assembly is worn. This will avoid the sensation of the device acting as an ear plug, and will be more conducive to wearing the earpiece for an extended period of time (e.g., hours, days or longer). As indicated in FIG. 2B and as seen in FIGS. 2E and 2F, the second body 206 has a central opening 208 therethrough. The opening 208 may be defined by one or more interior sidewalls of the second body. FIG. 3 illustrates a cutaway view 300 of the second body, in which it can be seen that the opening 208 extends generally along longitudinal axis 302 for sound to pass through. While one large opening is shown, multiple smaller holes may be provided.

In one example, the opening is formed as part of the housing of the second body, and remains open after insertion into the ear canal. In another example, one or more tubes of a non-collapsible (rigid or semi-rigid) material may be inserted into or fabricated as part of the second body's housing. In this case, the tubes would prevent pinching or crimping of the housing material (e.g., foam or silicone), allowing the wearer to hear ambient sounds without appreciable distortion (e.g., without cutting off or attenuating higher frequencies beyond 10-15 kHz) or reduction in volume. In one example, in place of or in addition to the opening(s), a small speaker may be incorporated into the housing of the second body. In this scenario, the speaker would provide sound to the inner portions of the ear canal. The speaker may be configured to emit sounds in place of or to augment sounds passed through the opening(s).

Also shown in cutaway view 300 of FIG. 3 is an end portion of the flexure. In this example it can be seen that the interior 304 of the flexure is hollow or otherwise includes an opening therealong. The central region of the flexure may be hollow, for instance, to run one or more wires or cables between the first and second bodies.

Figure 4:
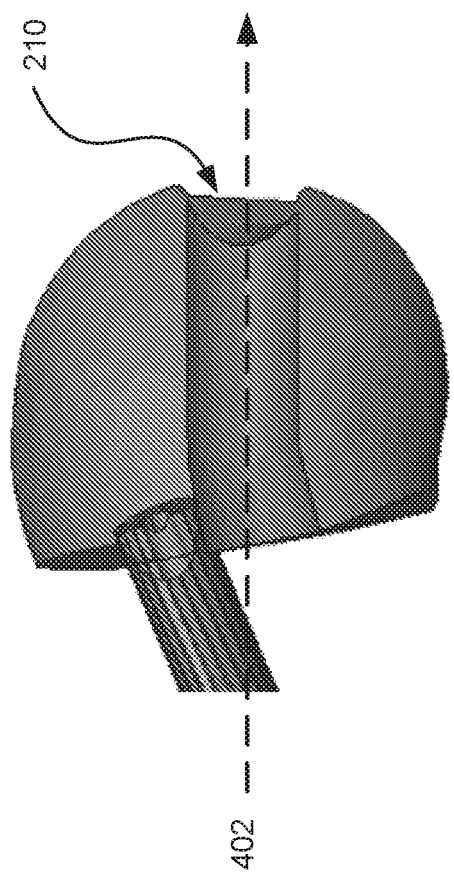
FIG. 4 illustrates a cross-sectional view of another body of the earpiece of FIGS. 2A-H in accordance with aspects of the technology.

Similarly, as shown FIGS. 2B, 2E-F and in cutaway view 400 of FIG. 4, the first body may also have an opening 210 therethrough, for instance extending generally along longitudinal axis 402. Unlike the opening 208, the opening 210 is not used to conduct sound, since the first body is not disposed adjacent to the ear canal. Rather, in one example the opening 210 may allow the first body to compress or otherwise conform to the available space of the cymba conchæ (or another part of the ear).

Figure 5B:
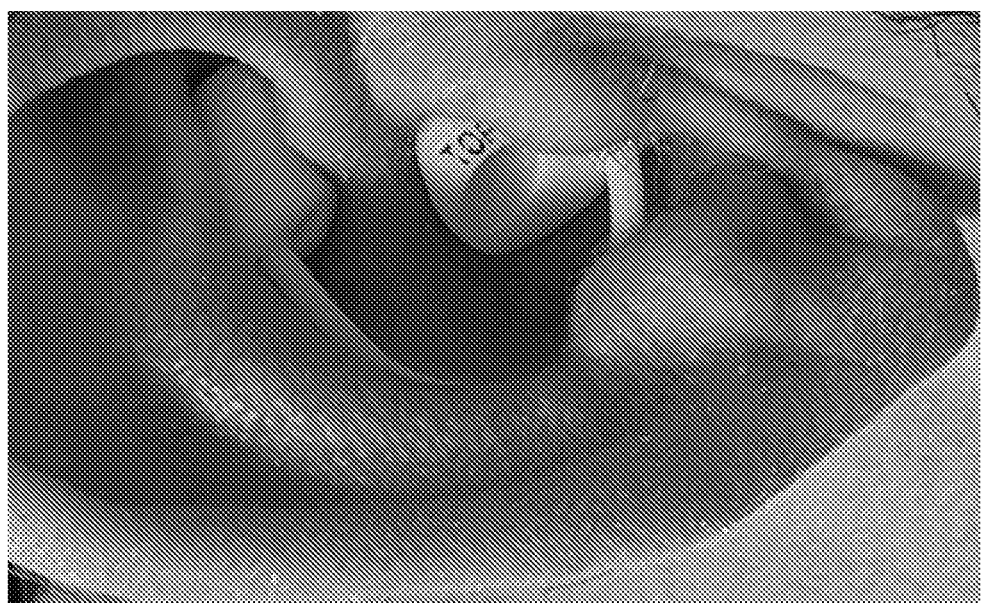
FIGS. 5A-B illustrate example in-ear placements of a multi-body earpiece in accordance with aspects of the technology.
Figure 5A:
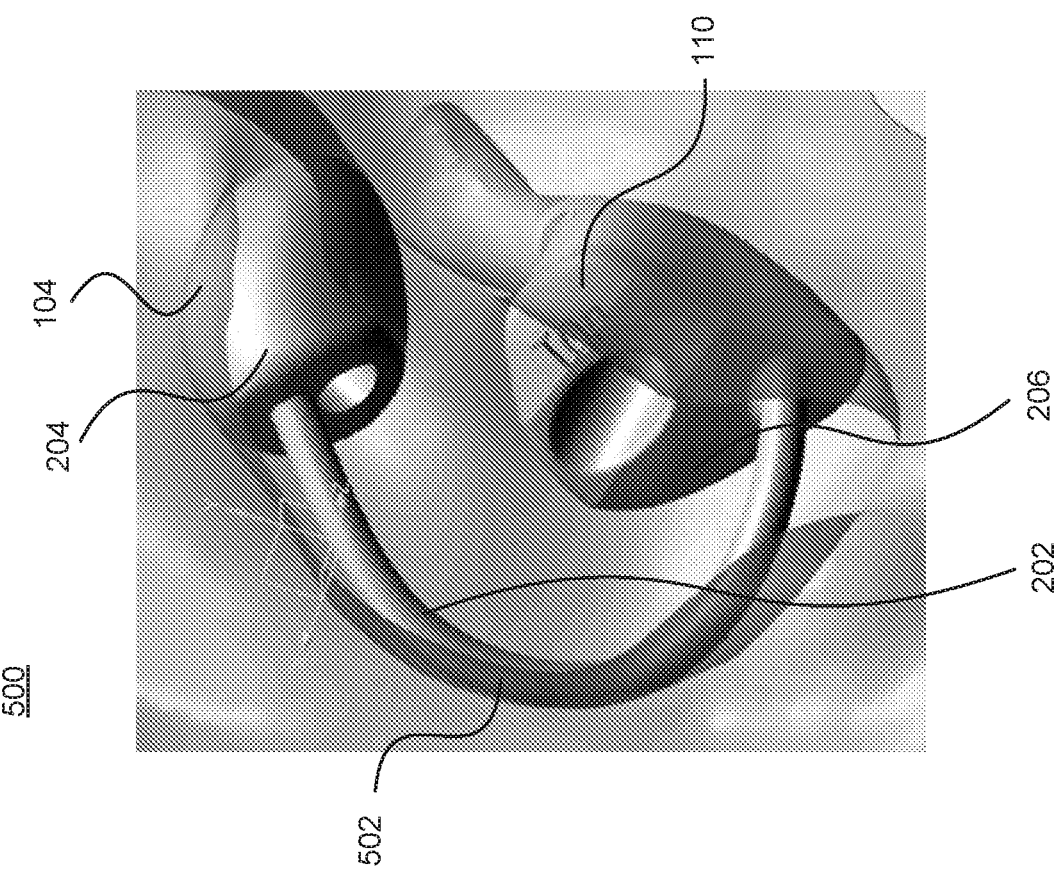

FIGS. 5A-B illustrate examples of the multi-body earpiece structure arranged in the ear. As seen in the partial see-through view 500 of FIG. 5A and the photographic view 510 of FIG. 5B, the first body 204 is received within the cymba conchæ region and at least partly covered by a fold of the antihelix, while the second body 206 is configured to be received by the opening to the ear canal. And the second body 206 is inserted into the opening of the ear canal and is partly covered by the tragus. As shown in both figured, the flexure 202 contours along the outer perimeter of the concha, and is partly enclosed by a fold of the antihelx.

This positioning within the outer ear provides the earpiece with multiple points of contact along both the first and second bodies as well the flexure. In one scenario, this configuration may act as a natural leaf spring to provide a spring force, which helps maintain the earpiece in contact with different points along the outer ear. In particular, the flexure and bodies are able to push against the skin, for instance at different locations (anchor points) about the antihelix, concha and/or opening to the ear canal, while also being able to flex or otherwise move as different parts of the ear move. The flexure adds an additional point (or set of points) of contact that helps to lock the two bodies in place. This creates a triangulated set of contacts that holds the earpiece in place to minimize movement. Pushing against the ear in this way can actually make things more comfortable for the wearer, and also provide better sensor connections for measurement purposes. Also, the general arcuate shape can help self-center the device when placed in the ear.

This architecture allows for an increased size of the auditory channel along the body 206 to mitigate sound occlusion. For instance, the sidewall(s) of the body 206 do not need to be very thick because the body 206 does not have to secure itself alone to the ear. The configurations of the two bodies can be either derived from a scan of a person's ear (custom), or be non-derived bodies for a more universal type fit and product. In the latter case, foam, silicone and/or other compressible or malleable materials may be employed. By way of example, some arrangements may have sidewalls that are as thin as 0.75 mm in wall thickness from the exterior of the body to an interior channel. These may be made from, e.g., silicone, or a silicone exterior with a plastic insert/interior in an overmold arrangement. In some instances, conductive foams can be used.

Figure 6C:
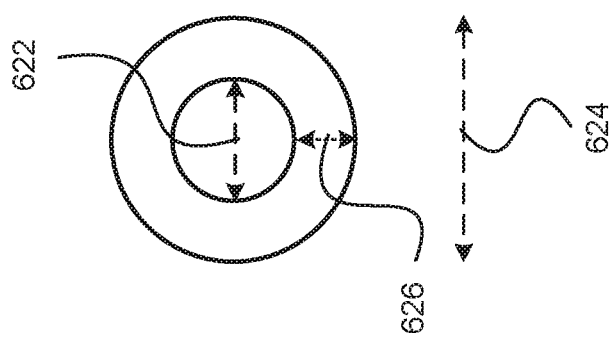
FIGS. 6A-C illustrate aspects of a flexure in accordance with aspects of the technology.
Figure 6B:
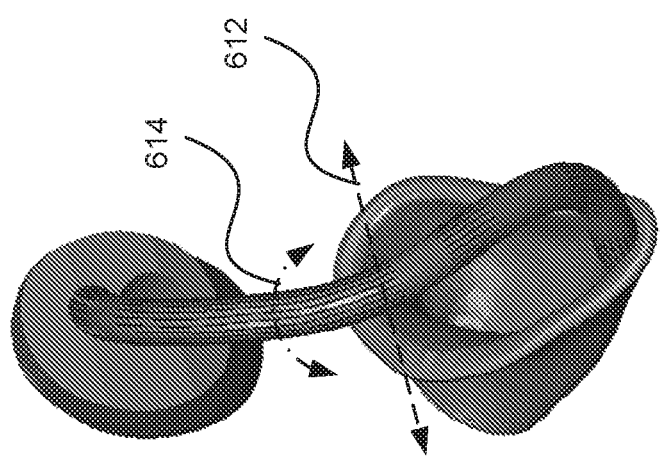
Figure 6A:
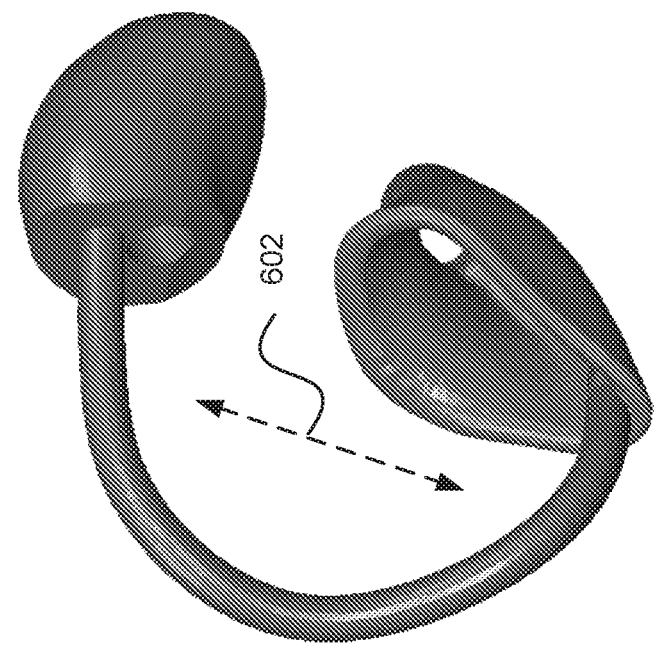

As noted above, the flexure body may be hollow, such as to carry wiring for, e.g., signals or power, between the two remote bodies. FIG. 6A presents a view 600, in which the dashed line 602 indicates that the ends of the flexure may move toward or away from one another. And FIG. 6B presents another view 610, in which the dashed line 612 indicates that the different portions of the flexure may move laterally (or in some other direction) or otherwise flex, and dash-dot line 614 indicates that one or more sections of the flexure may rotate. Changes in position, rotation or twisting, or other movement of the flexure may be in response to changes to the 3D shape of the ear as the wearer moves his or her head.

The relative rigidity or tension of the flexure helps to lock the two bodies in place. According to one aspect, the tension of the flexure may be tuned. In one example, the tuning may be accomplished by varying the length of the flexure. For instance, a default flexure length may be on the order of 3.0 cm-6.0 cm. Lengthening or shortening the flexure by 0.1-0.5 cm may correspondingly increase or decrease the tension. Alternatively or additionally, varying the diameter of the flexure may also change the tension or stiffness of the flexure. For instance, a thicker sidewall or larger overall diameter increases the stiffness, while a thinner sidewall or smaller overall diameter decreases the stiffness. As shown in cross-sectional view 620 of FIG. 6C, the flexure may have an inner opening 622 on the order of 0.3-0.8 mm, an outer diameter 624 on the order of 1.0 mm-2.5 mm, and a sidewall thickness 626 on the order of 0.1-1.2 mm. A spring wire, coil or other reinforcement may be run along the sidewall(s) of the flexure to provide the desired stiffness. By way of example only, the spring wire diameter can vary to tune the stiffness added to the flexure, such as between 0.02 mm up to 2 mm. Any or all of these approaches may be employed to tune the tension to increase or decrease the holding pressure and comfort, while ensuring that the bodies remain in place. In one scenario, the earpiece(s) may be supplied with a kit of flexures. Here, the flexures may be of different lengths, thicknesses, stiffnesses, colors, etc.

Fabrication

Multi-body earpiece structures such as described above can be fabricated using different combinations and/or layers of soft, semi-soft, and hard materials of varying durometers to achieve all the needs for fit and sensing. For instance, silicone, nylon, conductive polymers and other materials can be used at different locations along the bodies 204 and 206, as well as along the flexure 202. In one scenario, harder acrylic-like materials could be coated with softer bio-compatible materials to enhance comfort of either body for long-term wear. In one particular example, silicone is the primary bio-compatible material that may be over-molded on an acrylic base structure. Sensor contacts may be formed in or on the silicone, with wiring printed or otherwise run along the acrylic base. There are many electrically conductive metal materials that may be arranged to have contact with the skin for the sensors. A non-exhaustive list of such metals includes silver (Ag), silver chloride (AgCl), AgAgCl, gold (Au), platinum (Pt), titanium nitride (TiN), etc. Furthermore, colors for part or all of the sensor assembly may be selected so that the device is unobtrusive and blends in with the wearer's ear.

Different manufacturing approaches may be feasible for the multi-body earpiece. For instance, each body and the flexure can be fabricated as separate components and then snapped together or otherwise assembled. This might allow for a circuit board (or boards) to be inserted in each body during assembly, and for wiring or flexible circuits to be arranged along the flexure. Alternatively, 3D printing or injection molding may be employed. These techniques may provide greater flexibility when incorporating different materials. Here, the circuitry may be added as part of the manufacturing process as opposed to requiring additional assembly steps. In one example, the flexure and the two bodies may be integrally fabricated together of one or more layers of material via a 3D printing or injection molding process.

In one scenario, the multi-body earpiece architecture may be configured to amplify sound. For instance, one or more small microphones may be placed at selected points on the upper body 204 and/or the flexure 202. In this case, one or more speakers may be arranged along the lower body where it is positioned along the opening to the ear canal.

Figure 7B:
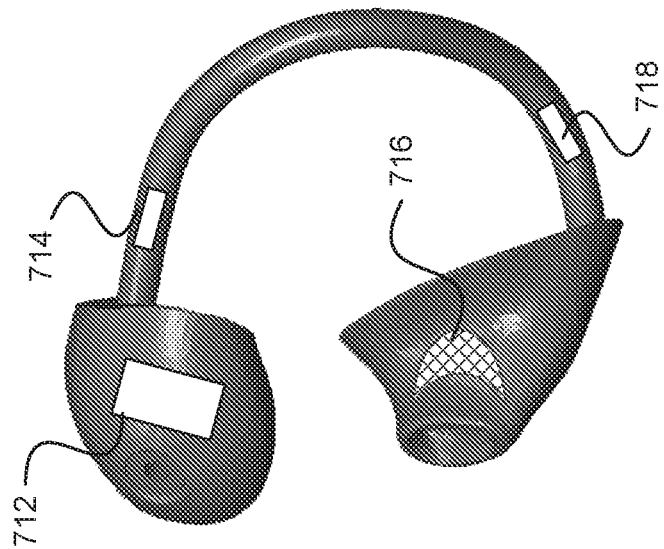
FIGS. 7A-B illustrate example sensor placement in accordance with aspects of the technology.
Figure 7A:
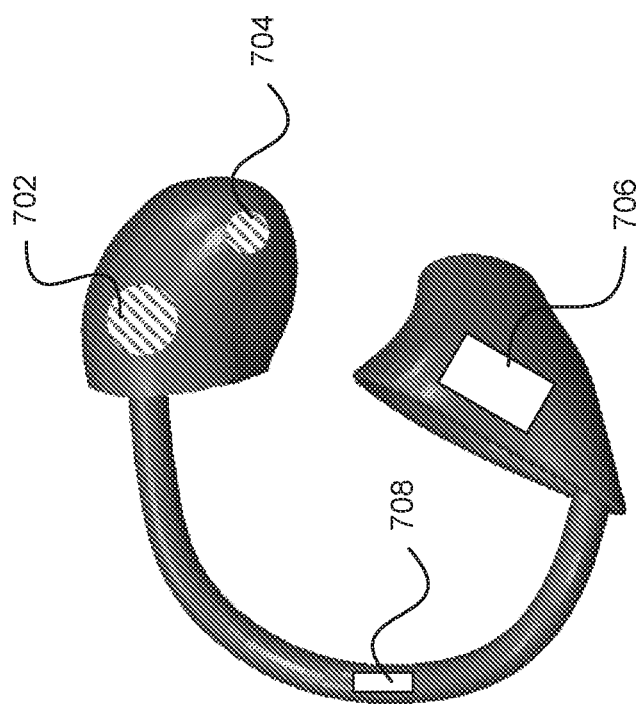

FIGS. 7A-B illustrate views 700 and 710, in which various sensors 702-708 and 712-718, respectively, are arranged at various positions of the two bodies and the flexure. In one example the sensors are only arranged along one or both of the bodies. In another example, sensors may also be disposed along the flexure. By way of example only, the sensors may include EEG sensors, MEG sensors, heart rate sensors, temperature sensors, electrodermal activity (EDA) sensors, pulse oximeter sensors, a glucometer, orientation sensors, location sensors, inertial measurement units (e.g., accelerometers), optical or infrared sensors, etc., which can be employed in any combination. Certain sensors can be disposed anywhere along the multi-body earpiece, such as orientation, location and/or IMU sensors. In contrast, other sensors could be placed in contact with one or more portions of the ear to benefit from direct contact with the underlying tissue. Such "contact" sensors may have preferred locations along the ear that have better electrical conductivity to the brain, better local blood flow, better acoustics, etc. In other examples, more than two bodies may be employed to provide additional points of contact along different parts of the outer ear and/or the back of the ear.

Example Systems

For sensors to pick up signals of interest with high fidelity while rejecting or minimizing noise, according to one aspect of the technology the multi-body earpiece includes a minimum of two electrodes. For example, a first electrode may be placed as close to the brain as possible, for instance along the upper body 204 within the cymba conchæ region. A second electrode can be placed such that it detects the same types of signals as the first, e.g., on the flexure along the outer perimeter of the concha, but potentially with some attenuation of the desired signal. This approach allows a differential amplifier to reject common mode interference. A third electrode could be place relatively far from the first and/or second electrodes, for instance on the lower body 206 adjacent to the opening of the ear canal, or potentially at a different location on the other ear. Here, the third electrode may be used as a "right leg drive" (RLD) to hold the other two electrodes at a known potential relative to the sensing electronics. Furthermore, another portion of the earpiece may include an additional body or flexure may provide an additional point of contact. In one scenario, the earpiece may have a portion wrapping around the back of the ear (e.g., coming out of the helix body and over the top of the ear) to an additional body that houses more electronics, and also has another sensor that could be placed on otherwise in operative engagement to the mastoid.

As noted above, FIGS. 7A-B illustrate examples of how bio sensors tor EEG, EMG, ECG or other testing may be arranged on the multi-body earpiece. By way of example, the different sensor contacts (e.g., electrodes or other sensors) 702-708 and 712-718 may be arranged on different sides of the device. As shown, the contacts, which may be any of the electrically conductive metal materials described above, can have different shapes, orientations and placements. The locations and configurations as shown are merely exemplary and may vary depending on the specific earpiece structure, the type(s) of signals to be detected, placement of other components, etc.

While the above examples show a multi-body earpiece for one ear, in some scenarios it is desirable to have sensor assemblies worn in both ears. Dual-ear arrangements may provide information that is local to one ear (e.g., a mono left/right auditory system), or that can best be seen with widely spaced electrodes (e.g., across/thru the head for EEG analysis). Dual-ear arrangements may also provide indications that received signals are in fact common to both ears and are thus not locally produced (e.g., ECG).

Upon insertion of the multi-body earpiece(s) into the ear(s), the sensor assembly(ies) is configured to detect Alpha waves or other waves via the bio-sensors. Processing of such signals may be performed at the sensor assembly, by a remote processing system, or both.

Figure 8A:
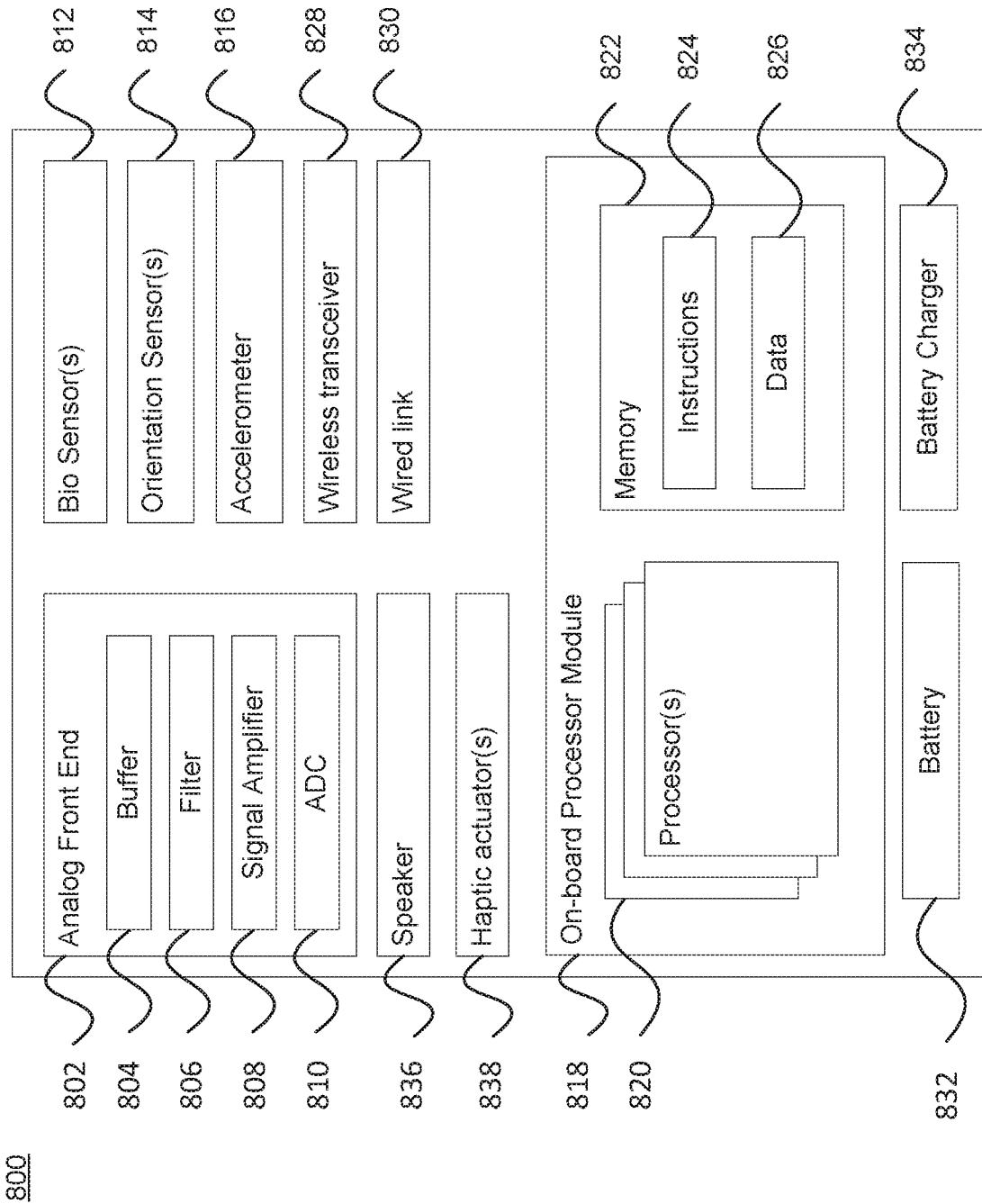
FIG. 8A illustrates an in-ear sensor assembly in accordance with aspects of the technology.
Figure 8B:
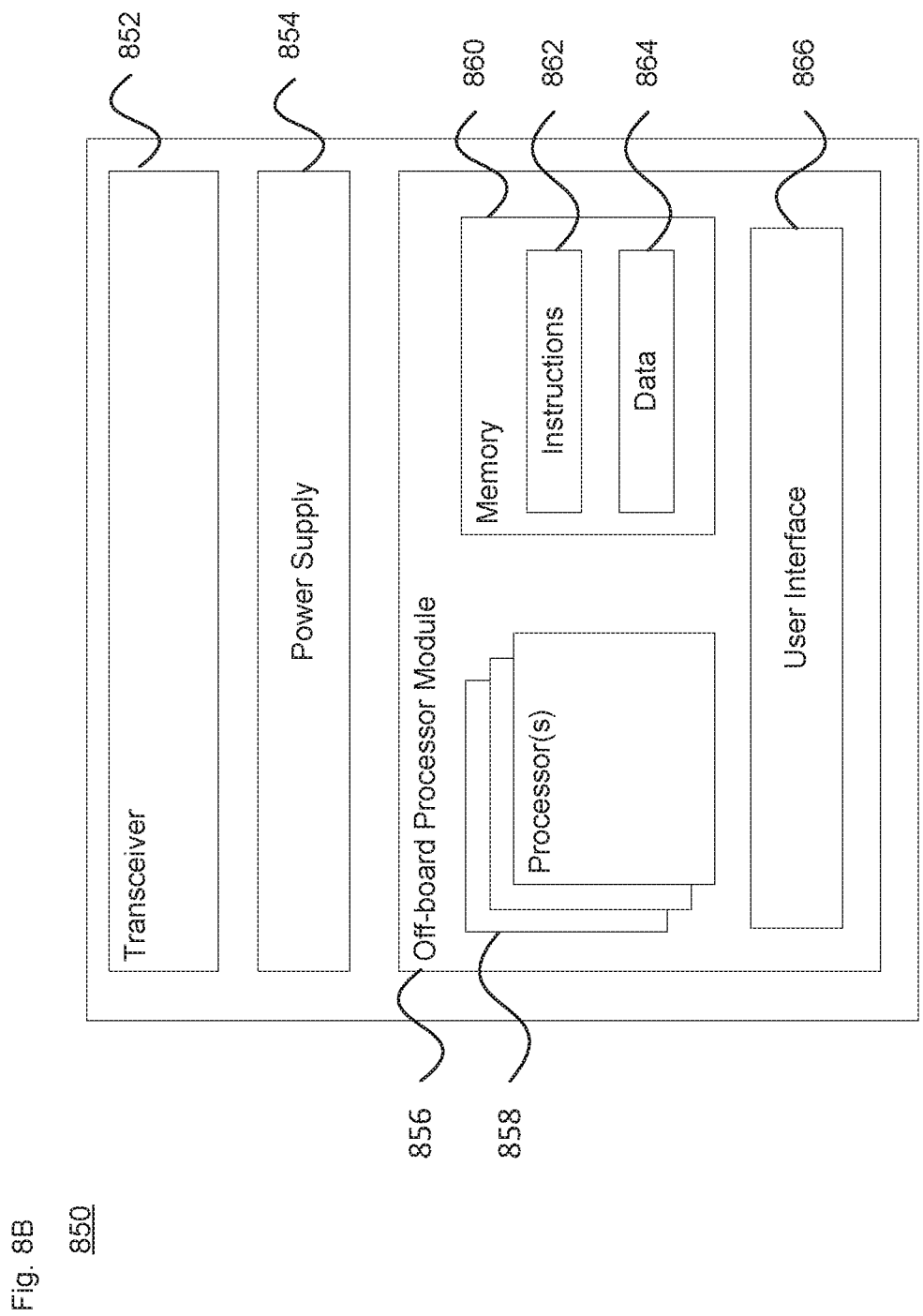
FIG. 8B illustrates an external processing system in accordance with aspects of the technology.

FIG. 8A illustrates one example of an on-board processing system 800, and FIG. 8B illustrates one example of a remote processing system 850. In this example, the signals from the sensor contacts may first be received by an analog front end (AFE) 802. The AFE 802 may provide one or more of signal buffering via buffer 804, filtering via filter(s) 806, signal amplification by amplifier 808, and/or analog to digital conversion by analog to digital converter (ADC) 810.

The processing system 800 may also receive biometric and other information from additional bio sensors 812, such as temperature, heart rate, EDA/galvanic skin response, pulse oximeter, glucometer and/or other sensors. Other sensors may include one or more orientation sensors 814 and an accelerometer 616. Some or all of the information from these other sensors may also be processed by AFE 802.

The processing system 800 may analyze the obtained data with an on-board processor module 818, which includes one or more processors 820 as well as memory 822 that stores instructions 824 and data 826 that may be executed or otherwise used by the processor(s) 820. The one or more processors 820 may be, e.g., a controller or CPU. Alternatively, the one or more processors 820 may be a dedicated device such as an ASIC, FPGA or other hardware-based device. The memory 822 may be of any type capable of storing information accessible by the processor(s) in a non-transitory manner, such as solid state flash memory or the like.

The instructions 824 may be any set of instructions to be executed directly (such as machine code) or indirectly (such as scripts) by the processor(s). For example, the instructions may be stored as computing device code in the non-transitory memory. In that regard, the terms "instructions" and "programs" may be used interchangeably herein. The instructions may be stored in object code format for direct processing by the processor(s), or in any other computing device language including scripts or collections of independent source code modules that are interpreted on demand or compiled in advance. The data 826 may be retrieved, stored or modified by one or more processors in accordance with the instructions 824. As an example, data 826 may include heuristics to be used when calibrating or evaluating electrode viability, for instance to rank electrode suitability based on signal-to-noise ratio or other metrics.

Alternatively or in addition to on-board signal analysis, the processing system may transmit the obtained data to remote processing system 850. This may be done, for instance, via a wireless transceiver 828 or a wired link 830, such as I2C, SPI, Universal Asynchronous Receiver/Transmitter (UART), I2S, or some other low-signal count communications path. In the former case, the wireless transceiver 828 may communicate with the remote processing system 850 via Bluetooth™, Bluetooth™ LE, near field communication (NFC) or some other wireless communication method. In the latter case, a flexible printed circuit or other wired link 830 may extend out the end of the sensor assembly and be physically coupled to remote processing system 850 that can receive and/or process the obtained bio signals.

System 800 also includes a battery 832 to power the components of the system. It may also include a battery charger 834. The battery charger may be contactless, or may be plugged into an external power source to charge the battery.

In one example a speaker 836 may be incorporated into the system 800. The speaker 836 is operatively coupled to the on-board processor module 818 to provide sound to the inner portions of the canal. The module 818 may actuate the speaker 836 to supplement (augment) sounds passed through the ear canal, or to generate different sounds such as audible cues (e.g., tones) to provide information or give aural feedback to the wearer. Alternatively or additionally, one or more haptic actuators 838 may be employed to give haptic feedback or other physical sensations to the wearer.

The system 800 may be incorporated into or mounted on the multi-body earpiece as a monolithic integrated circuit or as a set of discrete components. For instance, the on-board processing system could be integrated into one or both of the two bodies of the earpiece and/or along the flexure. By way of example only, the AFE 802, sensors 812, 814 and 816, the battery 832, the battery charger 834, the speaker 836 and/or the haptic actuator(s) 838 need not be co-located with the on-board processor module 818. Rather, the individual components can be distributed across the earpiece, for instance based on their size and shape, and whether they can be arranged on planar or non-planar portions of the earpiece. Certain components may be added as different layers or regions of the earpiece are being formed, for instance by 3D printing.

According to one scenario, a given earpiece architecture combines the data collection from the various sensors with on-board processing and data link/storage elements. However, in other scenarios the earpiece architecture may primarily gather sensor data and transmit it off-board for processing.

Turning to FIG. 8B, as shown remote processing system 850 includes a transceiver 852. The transceiver 852 is configured to communicate with one or both of wireless transceiver 828 and wired link 830. The system 850 also includes a power supply 854, which may include batteries and/or a connection for an outlet or the like. The information received from the on-board processing system 800, whether raw or unprocessed, is passed from the transceiver 852 to the off-board processor module 856.

The off-board processor module 856 is configured to analyze the obtained data with one or more processors 858 as well as memory 860 that stores instructions 862 and data 864 that may be executed or otherwise used by the processor(s) 858, in a manner similar to described above. The one or more processors 858 may be, e.g., a controller or CPU. Alternatively, the one or more processors 858 may be a dedicated device such as a DSP, an ASIC, FPGA or other hardware-based device. The memory 860 may be of any type capable of storing information accessible by the processor(s) in a non-transitory manner, such as solid state flash memory, hard disc, optical medium or the like. The off-board processor module 856 may also include a user interface subsystem 866, which may be used to present information regarding the processed data to the wearer, a technician, doctor or other authorized user.

As noted above, it may be desirable for the multi-body earpiece(s) to be worn for extended periods of time. This can provide a wealth of information that can be used for different purposes. For instance, one could evaluate temperature, including heat exchange between two points, as well as heat expulsion. The temperature may vary depending on whether the wearer is sleeping, sitting, moving, etc. Different kinds of brain activity can be measured and compared to what else is going on with the body.

In one test scenario, the sensor assembly could send sound through the ear, possibly in a manner that is not perceptible to the wearer, and measure the resultant brain activity. Information about heart rate variability or actions (e.g., chewing) can also be collected. Any or all of this information can provide context regarding the wearer's overall health. For instance, the information can be compared to a baseline for the particular wearer, which can be used as an assessment tool. In one particular example, one could evaluate the brain wave base line, plus voice analysis, plus heart rate and/or other signals for assessing mental health, the possibility of a stroke, a neurological condition, etc. The results of the assessment could be used for immediate treatment or to set up a treatment program (e.g., to help with anxiety or helping an autistic patient to focus on someone speaking to them.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements. The processes or other operations may be performed in a different order or simultaneously, unless expressly indicated otherwise herein.

The invention claimed is:

1. A multi-body earpiece assembly configured for partial or complete insertion in an ear of a wearer, the multi-body earpiece assembly provides a stable arrangement that is both securely and comfortably maintained in the ear, the multi-body earpiece assembly comprising:
   a first body configured to be at least partly received within a cymba concha region of the ear, wherein the first body comprises one or more of an Electroencephalogram (EEG) sensor and a Magnetoencephalography (MEG) sensor;
   a second body configured to be received along an opening to an ear canal;
   a flexure coupled to the first body at a first end of the flexure and to the second body at a second end of the flexure, wherein each of the first body, the second body and the flexure provides a point of contact along a different portion of the ear to retain the multi-body earpiece assembly in an operational position;

wherein the flexure is configured to conform to a portion of a concha along an underside of an antihelix of the ear when in the operational position;

wherein the flexure adds an additional point of contact with skin of the ear for locking the first body and the second body in place, and wherein the flexure creates a triangulated set of contacts that holds the multi-body earpiece assembly in place to minimize movement and thereby providing the stable arrangement in the ear; and one or more sensors disposed along the multi-body earpiece assembly, the one or more sensors being configured to detect bio-signals and alpha waves via the ear of the wearer, wherein the one or more sensors comprises one or more of the EEG sensor and the MEG sensor.

2. The multi-body earpiece assembly of claim 1, wherein the one or more sensors are disposed along the first body, the second body, and the flexure; and wherein the one or more sensors further comprises one or more of an electrodermal activity (EDA) sensor, a heart rate sensor, a temperature sensor, a pulse oximeter sensor, a glucometer, an orientation sensor, a location sensor, inertial measurement units (e.g., accelerometers), an optical or infrared sensor.

3. The multi-body earpiece assembly of claim 1, wherein the second body is configured to avoid sound occlusion when the multi-body earpiece is worn in the ear of the wearer.

4. The multi-body earpiece assembly of claim 3, wherein a housing of the second body defines a central opening therethrough to avoid the sound occlusion.

5. The multi-body earpiece assembly of claim 1, wherein the flexure is configured so that the first and second ends are moveable toward and away from one another.

6. The multi-body earpiece assembly of claim 5, wherein the flexure is arranged to flex or rotate while conforming to a portion of the concha along the underside of the antihelix of the ear.

7. The multi-body earpiece assembly of claim 1, wherein the flexure has a hollow interior from the first end to the second end.

8. The multi-body earpiece assembly of claim 1, wherein the flexure has a tension that is tunable by adjusting a length of the flexure.

9. The multi-body earpiece assembly of claim 1, wherein the flexure is a separate component insertable into the first body and the second body.

10. The multi-body earpiece assembly of claim 9, wherein a tension or stiffness of the flexure is tunable based on a thickness of the flexure.

11. The multi-body earpiece assembly of claim 1, further comprising:

circuitry attached to one or more of the first body, the second body and the flexure;

wherein the circuitry is operatively coupled to the one or more sensors, the circuitry including a processing device configured to receive the detected bio-signals from the one or more sensors and to perform on-board processing of the received bio-signals or to transmit the received bio-signals to a remote processing system.

12. The multi-body earpiece assembly of claim 1, wherein the multi-body earpiece is formed of multiple materials including a first material having a first hardness and a second material having a second hardness less than the first hardness.

13. The multi-body earpiece assembly of claim 12, wherein the multiple materials includes one or more biocompatible materials arranged along the first body and the second body.

14. A sensor system configured to detect and process bio signals of the wearer, the sensor system comprising:

the multi-body earpiece assembly of claim 1; and a remote processing system including a transceiver configured for communication with a transceiver of the multi-body earpiece assembly, and one or more processors configured to process the bio signals received from the multi-body earpiece assembly.

15. The sensor system of claim 14, wherein the sensor system includes a pair of multi-body earpieces assembly of claim 1, wherein a first one of the pair is configured for insertion into one ear of the wearer and a second one of the pair is configured for insertion into the other ear of the wearer.

16. The sensor system of claim 14, wherein the one or more sensors are disposed along the first body and the second body, and the flexure; and wherein the one or more sensors further comprises, one or more of an electrodermal activity (EDA) sensor, a heart rate sensor, a temperature sensor, a pulse oximeter sensor, a glucometer, an orientation sensor, a location sensor, inertial measurement units (e.g., accelerometers), an optical or infrared sensor.

17. The sensor system of claim 14, further comprising:

circuitry attached to one or more of the first body, the second body and the flexure;

wherein the circuitry is operatively coupled to the one or more sensors, the circuitry including a processing device configured to receive the detected bio-signals from the one or more sensors and to perform on-board pre-processing of the received bio-signals prior to transmission to the remote processing system.

18. The sensor system of claim 14, further comprising:

circuitry attached to one or more of the first body, the second body and the flexure;

wherein the circuitry is operatively coupled to the one or more sensors, the circuitry including a processing device configured to gather the detected bio-signals from the one or more sensors and transmit the gathered signals to the remote processing system.

* * * * *